(12) United States Patent
Stöckl (10) Patent No.: US 6,866,827 B2
(45) Date of Patent: Mar. 15, 2005

(54) PROCESS AND DEVICE FOR THE PARALLEL PREPARATION OF AT LEAST 4N OLIGONUCLEOTIDES

(75) Inventor: Ludwig Stöckl, Poing (DE)

(73) Assignee: Metabion Gesellschaft fur angewandte Biotechnologie mbH (DE)

( * ) Notice: Subject to any disclaimer, the term of this patent is extended or adjusted under 35 U.S.C. 154(b) by 708 days.

(21) Appl. No.: 10/040,082

(22) Filed: Oct. 26, 2001

(65) Prior Publication Data

US 2002/0120128 A1 Aug. 29, 2002

Related U.S. Application Data

(63) Continuation of application No. PCT/EP00/03916, filed on May 2, 2000.

(30) Foreign Application Priority Data

Apr. 29, 1999 (DE) .......................................... 199 19 607

(51) Int. Cl.[7] .............................. C07H 21/00; B01J 8/00; B01J 19/00
(52) U.S. Cl. ........................ 422/134; 422/105; 422/116; 422/130; 422/131; 536/25.3; 536/25.31
(58) Field of Search .................................. 422/105, 116, 422/130–131, 134; 536/25.3, 25.31, 25.32

(56) References Cited

U.S. PATENT DOCUMENTS

| | | | | |
|---|---|---|---|---|
| 4,728,502 A | * | 3/1988 | Hamill | 422/116 |
| 5,047,524 A | * | 9/1991 | Andrus et al. | 536/25.31 |
| 5,053,454 A | * | 10/1991 | Judd | 525/54.11 |
| 5,368,823 A | * | 11/1994 | McGraw et al. | 422/134 |
| 5,462,748 A | * | 10/1995 | Lloyd et al. | 424/484 |
| 5,472,672 A | * | 12/1995 | Brennan | 422/131 |
| 5,538,694 A | * | 7/1996 | Delius | 422/131 |
| 5,807,525 A | * | 9/1998 | Allen et al. | 422/131 |
| 5,866,342 A | * | 2/1999 | Antonenko et al. | 435/7.1 |
| 6,264,891 B1 | | 7/2001 | Heyneker et al. | |
| 6,270,730 B1 | * | 8/2001 | McLuen et al. | 422/131 |

FOREIGN PATENT DOCUMENTS

| | | |
|---|---|---|
| WO | WO 95/11748 | 5/1995 |
| WO | WO 98/57181 | 12/1998 |
| WO | WO 99/65602 | 12/1999 |
| WO | WO 00/18503 | 4/2000 |
| WO | WO 00/40330 | 7/2000 |

OTHER PUBLICATIONS

Baier et al., "Synthesis and Purification in a Single Column on a High-Throughput Automated Oligonucleotide Production System", *BioTechniques* 20:298–303 (Feb. 1996).

* cited by examiner

*Primary Examiner*—Arlen Soderquist
(74) *Attorney, Agent, or Firm*—Webb Ziesenheim Logsdon Orkin & Hanson, P.C.

(57) ABSTRACT

In a process and a device for the parallel preparation of at least 4n oligonucleotides, at least four inserts each with n reaction vessels are first arranged on a plate (16), each reaction vessel containing a nucleotide initiator base bound to an inert carrier. Particular operations are then carried out in parallel with one another at four stations (28, 30, 32, 34), and in particular a deblocking operation simultaneously in all n reaction vessels of the insert at the first station (28), a first washing operation simultaneously in all n reaction vessels of the insert at the second station (30), a coupling operation in all n reaction vessels of the insert at the third station (32), and, simultaneously in all n reaction vessels of the insert at the fourth station (34), a second washing operation followed by a capping operation followed by a third washing operation followed by an oxidation operation followed by a fourth washing operation. The plate (16) with the inserts is rotated station by station, the above-mentioned operations being carried out, until the desired oligonucleotides have been formed by coupling individual nucleotides to one another.

29 Claims, 4 Drawing Sheets

PROCESS AND DEVICE FOR THE PARALLEL PREPARATION OF AT LEAST 4N OLIGONUCLEOTIDES

CROSS-REFERENCE TO RELATED APPLICATIONS

This application is a continuation of International Patent Application Number PCT/EP00/03916 filed on May 2, 2000, entitled "Method And Device For the Parallel Manufacture Of Oligonucleotides" and designating, inter alia, the United States, which claims priority to German Patent Application Serial No. 199 19 607.9, filed Apr. 29, 1999.

BACKGROUND OF THE INVENTION

1. Field of the Invention

The present invention relates to a process and a device for the parallel preparation of at least 4n oligonucleotides.

2. Description of the Related Art

DE 42 06 488 A1 discloses a process and a device for the preparation of oligonucleotides. The known device has four bars one above the other, the contact surfaces of which are worked by grinding and polishing such that the bars can be displaced relative to one another without a gap. One of the bars contains reactions spaces which can be filled and emptied via entry and exit lines in the other bars. The individual reaction spaces are filled successively with reagents. In order for the said contact surfaces of the displaceable bars to be sealed well with respect to one another, very precise working of these contact surfaces is necessary and the bars must be made of wear-resistant material, for example of stainless steel or of particular glass materials.

The demand for oligonucleotides is increasing constantly and there is therefore the desire to prepare the highest possible number of oligonucleotides inexpensively, in a short time and with a high quality. The oligonucleotides here can be the same or different.

The invention is therefore based on the object of providing an improved process and an improved device for the preparation of oligonucleotides which takes into account the abovementioned desire.

To this end the invention provides a process for the parallel preparation of at least 4n oligonucleotides. In the process according to the invention, at least four inserts each with n reaction vessels (n≧1) are arranged on or in a plate such that a first insert is at a first station, a second insert is at a second station, a third insert is a third station, and a fourth insert fourth station. Each reaction vessel contains an initiator base which is necessary for the synthesis of oligonucleotides and is bound, for example, to an inert carrier. Instead of an initiator base, it is also possible to use a so-called universal carrier known to experts. Porous glass, so-called controlled pore glass (CPG), can be used e.g. as the carrier material. A series of operations for oligonucleotide synthesis is then carried out in parallel at the four stations mentioned.

Thus, a so-called deblocking operation, by means of which protective groups present on the initiator bases are split off, so that individual nucleotide units can be coupled to the initiator base later, is carried out simultaneously in all n reactions vessels of the insert at the first station. These protective groups are also called DMT groups. Simultaneously with the deblocking operation taking place at the first station, a first washing operation by means of which the protective groups split off beforehand are washed out of the reaction vessels takes place at the second station, again simultaneously in all n reaction vessels at the second station. Also simultaneously with the two abovementioned operations, a so-called coupling operation by means of which the desired individual nucleotides are coupled on to the initiator bases or nucleotide chains in the reaction vessels takes place in all n reaction vessels at the third station. Again at the same time as the abovementioned three operations, a sequence of operations takes place simultaneously in all n reaction vessels of the insert at the fourth station, namely first a second washing operation, followed by a so-called capping operation, by means of which those oligonucleotides which have not undergone the desired chain lengthening in the preceding coupling operation are blocked in the reaction vessels, followed by a third washing operation, followed by an oxidation operation for stabilizing the phosphate foundation matrix of the oligonucleotides, and finally a fourth washing operation.

According to the invention, either the rotary plate is rotated station by station through the four stations mentioned, so that each insert passes through the individual stations in succession, or the stations are moved further by in each case one station relative to the inserts. This relative movement station by station between the inserts and the stations takes place until the desired oligonucleotides have been formed by coupling of the individual nucleotides to one another.

The synthesis cycle realized according to the invention by means of passing through the four stations is known per se and therefore does not need to be explained in detail. Nevertheless, by means of the process according to the invention this synthesis cycle is worked through in an extremely time-saving manner, in that firstly all n reaction vessels at a station are subjected simultaneously to the operation taking place at this station or to the operations taking place there, and in that secondly operations take place in parallel at all four stations. Furthermore, the process according to the invention utilizes in an intelligent manner the circumstance that the deblocking operation carried out at the first station and the coupling operation carried out at the third station are the operations which take the longest (and therefore determine the residence time required per station), by carrying out the significantly faster capping and oxidation operations successively at only one station (the fourth station).

The two measures mean that the process according to the invention is considerably faster compared with known processes for oligonucleotide synthesis. The productivity is increased in this manner, and the production costs for oligonucleotides can be lowered. Moreover, larger amounts of oligonucleotides can be provided in a shorter time. For example, if 24 reaction vessels are present per insert and if a period of time of 60 seconds is estimated as the cycle time per station, 96 oligonucleotides each with 20 nucleotide units can be produced within approx. 90 minutes. Assuming furthermore that a new run can be started about every 100 minutes, a production of 1,350 oligonucleotides per day is achieved with the process according to the invention. This corresponds to virtually 40 times the amount which can be prepared with the apparatus according to the abovementioned DE 42 06 488 A1.

SUMMARY OF THE INVENTION

According to a preferred embodiment of the process according to the invention, a monitoring operation which provides information on the quality of the deblocking operation carried out at the first station takes place at the second station together with the first washing operation carried out there. This monitoring operation is preferably carried out by means of an on-line measurement of the conductivity of a washing liquid used for the first washing operation. Alternatively, the monitoring operation can be carried out by means of an on-line measurement of the colour intensity of the washing liquid used for the first washing operation, measurement by means of UV light being used in particular. The wavelength of the UV light used preferably has a wavelength of 455–465 nm.

According to a particularly preferred embodiment of the process according to the invention, if the monitoring operation also takes place at the second station in addition to the first washing operation, the first washing operation is carried out until the monitoring operation shows that the protective groups removed in the preceding deblocking operation have been rinsed out completely. The term "completely" here is not to be understood in the absolute sense, but relates to the detection limit of the measurement method used in the context of the monitoring operation. The consumption of washing liquid is reduced by such a procedure, because on the basis of the continuous monitoring and evaluation of the washing liquid leaving the reaction vessels, the first washing operation can be ended immediately when the desired result is achieved. Furthermore, an increase in quality is achieved with such a procedure, since the first washing operation is not ended after a given period of time, but ending thereof depends on a particular result being achieved.

In the process according to the invention, a selected nucleotide base is advantageously added to the reaction vessels at the same time as an activator (catalyst) in the coupling operation carried out at the third station. This simultaneous addition of nucleotide unit and activator saves valuable time in an operation which, as mentioned above, determines the cycle time. Tetrazole is preferably used as the activator.

Furthermore, a marking group (label) which facilitates later identification of the oligonucleotide produced or of a product produced therefrom is also added, if desired, in the coupling operation carried out at the third station. The marking group is, in particular, a base analogue, a dyestuff or a hapten.

The process according to the invention is preferably designed as a flow-through process, i.e. the reaction vessels are constructed as flow-through vessels, for example in that each reaction vessel is closed by a frit base at the top and bottom. In a process designed in such a manner, the liquids to be fed to the reaction vessels (reagents, washing liquid etc.) are preferably conveyed into the individual reaction vessels and out of them by applying a pressure gradient between each reaction vessel inlet and each reaction vessel outlet. The pressure gradient can be generated either by an increased pressure in the reservoir containers for the reagents, washing liquids etc. or by applying a reduced pressure at the reaction vessel outlets. It is not absolutely necessary here for the inlet of each reaction vessel to be arranged at the top, but it is also entirely possible for it to be at the bottom, while the reaction vessel outlet is arranged at the top. Such an arrangement has the advantage that the liquids and reagents added to each reaction vessel from the bottom whirl up the carrier material, for example the glass beads, contained in the reaction vessels and in this manner allow better mixing of the liquid added in the reaction vessel.

The abovementioned object is also achieved according to the invention by a device for the parallel preparation of at least 4n oligonucleotides which has a first station for carrying out a deblocking operation, a second station for carrying out a first washing operation, a third station for carrying out a coupling operation and a fourth station at which a second washing operation, a capping operation, a third washing operation, an oxidation operation and a fourth washing operation are carried out in succession. The four stations mentioned are arranged in succession in the circumferential direction and are preferably the same distance from one another in the circumferential direction.

The device according to the invention furthermore comprises a plate in which at least four inserts each with n reaction vessels can be arranged such that a first insert is at the first station, a second insert is at the second station, a third insert is at the third station and a fourth insert is at the fourth station. The plate which accommodates the inserts is preferably constructed as a rotary plate which can be rotated station by station through the four stations mentioned. However, it is also possible to move the stations relative to the plate containing the inserts.

Each reaction vessel is constructed as a flow-through vessel with a reaction vessel inlet and a reaction vessel outlet arranged opposite, and is preferably arranged vertically. A liquid feed device is assigned to the reaction vessel inlets in each of the four stations. The feed device assigned to the third station preferably has n feed valves, so that a particular nucleotide unit can be added selectively to each reaction vessel. It is not necessary to provide the feed device with n feed valves in the other stations, since the operations which proceed there are carried out the with same reagents or liquids in respect of all the reaction vessels. However, under certain circumstances it is also desirable for the feed devices of the remaining stations to be provided with in each case n feed valves, for example if oligonucleotides of different lengths are to be produced. In fact, it is then possible to exclude the shorter-chain oligonucleotides which have already been finished from further unnecessary deblocking operations, in that the feed valves of the first station assigned to the corresponding reaction vessels are simply no longer opened. An unnecessary deblocking operation repeatedly carried out can in fact lead to a deterioration in the quality of oligonucleotides which have already been finished, because individual bases of the oligonucleotides are separated out, as a result of which the oligonucleotide in question is modified or destroyed. Furthermore, if the feed device of each station is provided with n feed valves, the consumption of reagents and other liquids can be minimized, because these are fed only to the reaction vessels in which they are actually required.

A drain channel into which the liquids emerging from the reaction vessels flow is assigned to each reaction vessel outlet in each station. The device according to the invention is constructed such that when the inserts are in a station, each reaction vessel inlet is in tight engagement with the associated feed device and each reaction vessel outlet is in tight engagement with the associated drain channel. According to one embodiment of the device according to the invention, the reaction vessel inlets are arranged at the top and the reaction vessel outlets are arranged at the bottom. However, the arrangement can also be reversed, so that the reagents and the other liquids are added to the reaction vessels from the bottom. This can be of advantage in respect of mixing in the reaction vessels.

When a relative movement by one station is carried out, there is a small axial distance at least between the reaction vessel inlets and the feed device or the feed valves. Wear on the sealing surfaces is significantly reduced in this manner, and there is nevertheless scarcely a possibility of access of undesirable substance to the reaction vessels.

According to one embodiment of the device according to the invention, the latter is in a sealed room with an inert gas environment, so that the oligonucleotide synthesis cannot be impaired by water or water vapour. The inert gas, for example argon or nitrogen, can advantageously be introduced continuously on to the device according to the invention from above, and then sinks down slowly over the device. The inert gas consumption is reduced in this manner, since only the device itself is surrounded by a protecting jacket of inert gas.

In one embodiment of the device according to the invention, there is also a small axial distance between the reaction vessel outlets and the drain channels while the relative movement station by station takes place. The device according to the invention is preferably constructed here such that all the liquid feed devices are accommodated in or on one valve-carrying panel and all the drain channels are accommodated in a suction panel. In this embodiment, the device according to the invention accordingly comprises as essential constituents three panels arranged one above the other, the middle panel of which is the plate. The valve-carrying panel and the suction panel have a flat contact surface to the plate and the reaction vessel inlets are preferably constructed flush with the upper side of the plate and the reaction vessel outlets are preferably constructed flush with the under-side of the plate, so that by merely placing the valve-carrying panel, the plate and the suction panel one on top of the other a tight connection can be obtained between the reaction vessels and the feed valves as well as the drain channels. For faultless and inexpensive sealing, for example, sealing rings of an elastomer material can be accommodated in the flat contact surface of the valve-carrying panel and the flat contact surface of the suction panel, these connecting each reaction vessel inlet tightly with the corresponding feed valve and each reaction vessel outlet tightly with the associated drain channel.

In a particularly preferred embodiment of the device according to the invention, the valve-carrying panel and the suction panel are fixed against rotation and the rotary plate and the suction panel can be lowered relative to the valve-carrying panel. To rotate the rotary plate by one station, the latter, together with the suction panel, is lowered slightly with respect to the valve-carrying panel, rotated by a station, and then raised again adjacent to the valve-carrying panel. The suction panel is lowered here somewhat further than the rotary plate, so that there is a small gap between the suction panel and the rotary plate and the seals present are not exposed to shear stress when the rotary plate is rotated. When the rotary plate is raised after rotation thereof, the suction panel is also moved tightly adjacent to the under-side of the rotary plate.

In an alternative embodiment of the device according to the invention, at least the liquid feed device of the third station has a plurality of individual feeds, each of which is in liquid connection with only one of the various liquids to be added to the reaction vessels at the station and the number of which corresponds to at least the number of different liquids to be added to the reaction vessels at the station. A coupling drive can connect each individual, feed with a reaction vessel inlet as required. The individual feeds are arranged on a common carrier which can be displaced at right angles to the reaction vessel inlets. The carrier is preferably constructed as a carriage which can be displaced position by position, each reaction vessel inlet representing a position.

Such a liquid feed device is advantageously constructed such that the coupling drive in one position of the carrier in which the individual feeds are in alignment with reaction vessel inlets connects to a reaction vessel inlet only that individual feed which is connected to precisely the liquid required in the reaction vessel in question, and such that, depending on the requirement, the carrier is then displaced optionally several times into another position in which the individual feeds are in alignment with reaction vessel inlets and in which in turn the coupling drive connects to a reaction vessel inlet only that individual feed which is connected to the liquid precisely required in the reaction vessel in question. A rational feeding of the liquids required in the individual reaction vessels is achieved in this manner, without mixing or entrainment of the various liquids being able to occur. This benefits the quality of the oligonucleotides prepared.

In all the embodiments of the device according to the invention, the inserts preferably extend radially in respect of the rotary plate, the reaction vessels being arranged in at least one row. To increase the capacity of the device according to the invention, each insert preferably has two rows of reaction vessels parallel to one another and extending radially.

The inserts of the device according to the invention are preferably made of plastic, in particular of PEEK (polyether ether ketone). In the device according to the invention it is not necessary to produce the inserts from high-grade steel or from glass ceramic, since the inserts are not subjected to abrasion.

According to a preferred embodiment, each insert is constructed such that it has on its longitudinal sides at least one coding groove and/or one coding projection. The coding groove of one insert cooperates with a coding projection of complementary shape of the rotary plate and a coding projection of the insert cooperates with a coding groove of complementary shape of the rotary plate. On each insert, at least the coding groove or the coding projection is constructed differently from the other inserts, so that a particular insert can be inserted into the rotary plate only at a particular position. The inserts can also have a plurality of coding grooves and/or coding projections.

The coding grooves and coding projections of the inserts are preferably constructed such that all the inserts of a device according to the invention can be assembled to reaction vessel panels, for example to reaction vessel panels in MTP format. Further handling of the oligonucleotides prepared by means of the device according to the invention is simplified in this manner.

In an advantageous embodiment of the device according to the invention, the reaction vessel outlet and/or the reaction vessel inlet of each reaction vessel has a constriction point which can be closed by a movable ball. The ball is preferably pushed in the direction of the constriction point by the force of gravity, by the force of a spring or by magnetic force.

The process according to the invention is explained in more detail with the aid of an embodiment example of the device according to the invention with reference to the attached figures in diagram form.

DESCRIPTION OF THE PREFERRED EMBODIMENTS

Figure 1:
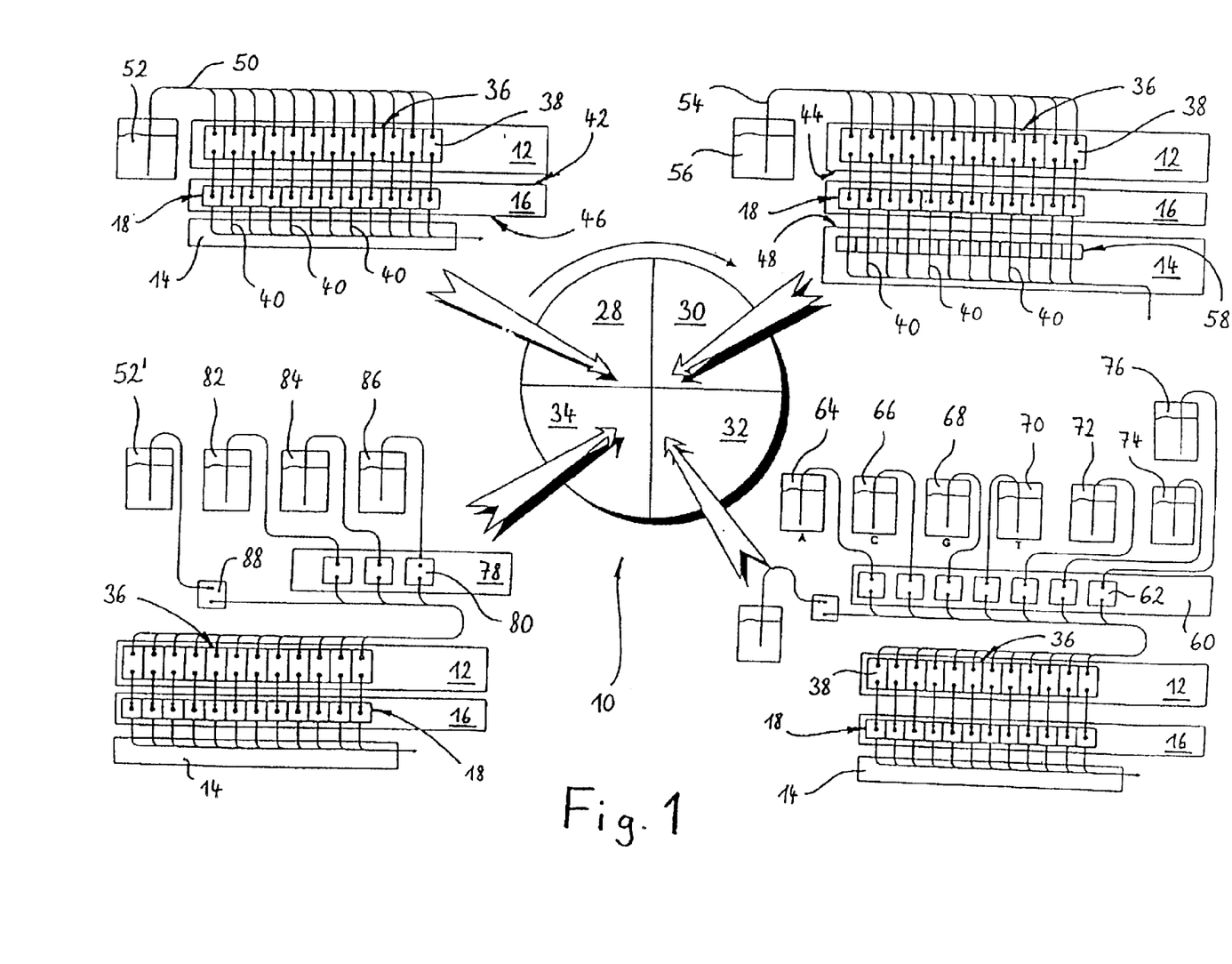
FIG. 1 shows a functional diagram of an embodiment example of a device according to the invention for the parallel preparation of 96 oligonucleotides.

FIG. 1 shows in the middle, in diagram form, a device 10 for the parallel preparation of 96 oligonucleotides. Essential constituents of the device 10 are three panel-like structures arranged one above the other, namely a valve-carrying panel 12 arranged at the top, a suction panel 14 arrange at the bottom and a rotary plate 16 arranged between these two panels. This rotary plate 16 can be rotated relative to the valve-carrying panel 12, which is fixed against rotation, and the suction panel 14, which is also fixed against rotation.

Figure 2:
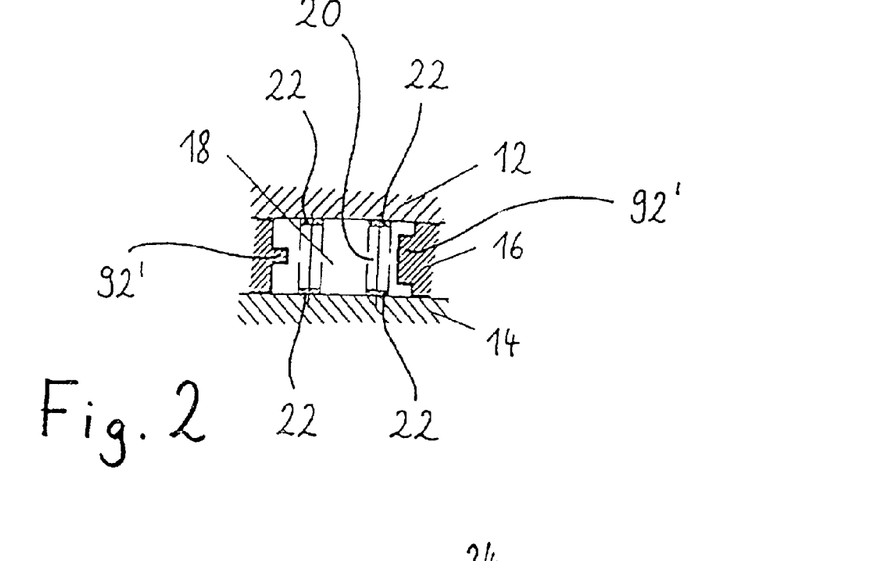
FIG. 2 shows an insert used in the device according to the invention in the state in the device.

In the rotary plate 16 are four removable inserts 18, each provided with twenty-four reaction vessels 20 arranged in two parallel rows of twelve reaction vessels 20 (see FIG. 2). Each reaction vessel 20 is closed at the top and bottom by a frit base 22 and contains glass beads of CPG (controlled pore glass), to which the particular initiator bases are bound. Each reaction vessel 20 has a reaction vessel inlet 24 at the top and a reaction vessel outlet 26 at the bottom. The four inserts 18 are arranged in the circular rotary plate 16 at a distance of in each case 90° to the next insert 18 such that they can be inserted into the rotary plate 16 and pulled out of it radially.

The device 10 has four separate stations 28, 30, 32, 34, at which particular operations necessary for oligonucleotide synthesis are carried out. The stations 28, 30, 32 and 34 follow one another in the direction of rotation r of the rotary plate 16 at a distance of in each case 90°. At each station 28, 30, 32, 34 a liquid feed device 36 with twenty-four feed valves 38 is arranged in or on the valve-carrying panel 12 such that a feed valve 38 is assigned to each reaction vessel inlet 24. At each station 28, 30, 32, 34, below each reaction vessel outlet 26 a drain channel 40 is furthermore provided in the suction panel 14, through which liquid emerging from the associated reaction vessel 20 is removed.

The rotary plate 16 can be lowered relative to the valve-carrying panel 12 by means of a lifting and lowering device, which is not shown. The suction panel 14 can also be lowered and raised again relative to the valve-carrying panel 12 with the same lifting and lowering device. Accordingly, the reaction vessel inlets 24 of all the reaction vessels 20 can be laid tightly against the assigned feed valves 38 and the drain channels 40 can be laid tightly against the assigned reaction vessel outlets 26 by means of the lifting and lowering device. In the embodiment shown, the rotary plate 16 has a flat upper side 42, which cooperates with a flat contact surface 44 of the valve-carrying panel 12, and a flat under-side 46, which cooperates with a flat contact surface 48 of the suction panel 14. The actual sealing between the upper side 42 of the rotary plate 16 and the contact surface 44 and between the under-side 46 of the rotary plate 16 and the contact surface 48 is achieved by O-rings of elastomer material which are arranged around each reaction vessel inlet 24 and each reaction vessel outlet 26 and are let either into the upper side 42 or the contact surface 44 and into the contact surface 48 or the under-side 46 of the rotary plate 16.

Functioning of the device 10 for oligonucleotide synthesis is explained in more detail in the following. It is to be assumed here that in each reaction vessel 20 there is a solid phase carrier (fine-grained CPG glass substrate) to which a first nucleotide (initiator base) is bound. Further nucleotides are to be bonded to this first nucleotide. It should be mentioned that each nucleotide to be added anew can couple with only one of its ends, the so-called 3' end, because its other end, the so-called 5' end, is provided with a protective group (DMT group), which prevents the nucleotides added anew to the reaction vessel 20 from reacting with one another.

Starting at a first station 28, in a so-called deblocking operation, the DMT groups (protective groups) are split of from the initiator nucleotide (or a nucleotide chain which has since been formed) bound to the solid phase carrier, in order to render the 5' end of the nucleotide strand reactive. The protective groups are split off by addition of TCA (trichloroacetic acid; more precisely 3% trichloroacetic acid in methylene chloride). To this end, the feed valves 38 of the first station 28, which are connected via a line 50 to a reservoir container 52 for TCA, are opened for 5 seconds and then closed again. The TCA solution added to the reaction vessels 20 then remains in the reaction vessels 20 for 50 seconds. The TCA solution is then sucked out of the reaction vessels 20 by applying vacuum to the drain channels 40 of the first station 28.

The rotary plate 16 and the suction panel 14 are then lowered until a small gap has formed between the upper side 42 of the rotary plate 16 and the contact surface 44 and between the under-side 46 of the rotary plate 16 and the contact surface 48. The rotary plate 16 is then rotated by 90° in the clockwise direction, so that the insert 18 with its reaction vessels 20 in the first station 28 at the start is now in the second station 30. The suction panel 14 and the rotary plate 16 are then again moved tightly adjacent to one another and to the valve-carrying panel 12.

A first washing operation takes place in the second station 30, during which the reaction vessels 20 are rinsed intensively. This is effected by addition of acetonitrile, for which the feed valves 38 of the second station 30, which are connected via a line 54 to an acetonitrile reservoir container 56, are opened. The acetonitrile solution runs through the reaction vessel inlets 24 into each reaction vessel 20 and out of the reaction vessel outlets 26 again into the drain channels 40 of the second station 30.

A measuring device 58 by means of which the quality of the deblocking operation which has taken place at the first station 28 can be checked on-line is integrated into the drain channels 40 of the second station 30. For this, the acetonitrile solution flowing out of the reaction vessels 20 can be investigated by measuring its conductivity or by measuring its colour intensity. For example, the protective groups removed in the deblocking operation can be detected optically as an orange coloration of the acetonitrile solution. If the measuring device 58 no longer detects such a coloration, it can be assumed that all the protective groups removed have been rinsed out of the reaction vessels 20. An addition time of 15 seconds is estimated to achieve this, but the acetonitrile solution is fed from the container 56 to the reaction vessels 20 by means of the feed valves 38 until coloration of the liquid leaving the reaction vessels can no longer be detected.

The rotary plate 16 is then rotated one station further as described above. The insert 18 in question is thus in the third station 32. The actual chain-lengthening reaction, which is called a coupling operation, takes place there. For the chain lengthening, a further nucleotide base must be added to the nucleotide chains in the reaction vessels 20, this then coupling to the nucleotide chain end which has been rendered reactive in the second station 30. For selection of the desired nucleotide base, the liquid feed device 36 assigned to the third station 32 is in fluid-carrying connection with a selector valve block 60, which has seven selector valves 62. One each of the selector valves 62 is connected to an adenosine reservoir container 64, a cytosine reservoir container 66, a guanosine reservoir container 68 and a thymidine reservoir container 70. A further selector valve 62 is connected to a reservoir container 72 for tetrazole, which serves as an activator. The two remaining selector valves 62 are connected with reservoir containers 74 and 76, which can contain, for example, marking reagents, say, or a dyestuff and hapten. Such marking reagents can be added during the coupling operation, in order later to allow identification of a product produced with the oligonucleotide.

By opening the selector valve 62 assigned to the desired nucleotide base and the corresponding feed valves 38, the nucleotide base selected can be added to the reaction vessels 20. About 2.5 seconds are estimated as the addition time. At the same time as the nucleotide base and/or shortly before and, if necessary, also thereafter, the activator is added to the reaction vessels 20 by opening the corresponding selector valve 62 (and the feed valves 38). The addition of the nucleotide bases and the activator is followed by a waiting time of about 30 seconds, in order to give the units to be added anew time to couple to the existing chain.

In the third station 32, the same nucleotide base, for example cytosine, can be added to all the reaction vessels 20. However, it is also possible for different nucleotide bases to be added to different reaction vessels 20, so that different oligonucleotide chains are produced in the various reaction vessels 20. This can be achieved in a simple manner by successive opening of the selector valves 62 which release the corresponding reservoir containers 64 to 70, always only the feed valves 38 assigned to those reaction vessels 20 into which the corresponding nucleotide base is to be introduced being opened. This successive feeding in of various selected nucleotide bases into different reaction vessels 20 presents no problem in terms of time, since the waiting time of 30 seconds required is still also ensured within the cycle time of 60 seconds if all four nucleotide bases are added.

After the waiting time has elapsed, the reaction solution in the reaction vessels 20 is sucked out through the drain channels 40 assigned to the third station 32. The rotary plate 16 is then rotated further by one station in the manner already described, so that the insert 18 in question is now in the fourth station 34.

In the fourth station 34, several operations take place in succession, namely a second washing operation, a capping operation, a third washing operation, an oxidation operation and a fourth washing operation. To this end, the liquid feed device 36 assigned to the fourth station 34 is in fluid communication with a second selector valve block 78 with three selector valves 80. The first of these selector valves 80 is connected to a reservoir container 82' for a first capping reagent, the second selector valve 80 is connected to a reservoir container 84 for a second capping reagent, and the third selector valve 80 is connected to a reservoir container 86 for an iodine solution. A washing liquid reservoir container 52', which can be identical to the reservoir container 52, can furthermore be connected in a liquid-carrying manner by a valve 88 to the liquid feed device 36 of the fourth station 34. By opening this valve 88 and all the feed valves 38 for about 15 seconds, acetonitrile solution is fed to all the reaction vessels 20 for carrying out the second washing operation. The acetonitrile solution runs through the reaction vessels 20 and into the drain channels 40 of the fourth station 34.

The first capping reagent contained in the reservoir container 82 and/or the second capping reagent contained in the reservoir container 84 are then fed to the reaction vessels 20 by closing the valve 88 and opening the corresponding selector valves 80 for about 3 seconds. The so-called capping operation carried out with these reagents is necessary, because never 100% of the oligonucleotide chains contained in the reaction vessels 20 have reacted in the preceding coupling operation with the nucleotide units to be added anew. Those chain ends which have not reacted as intended in the coupling operation must be blocked permanently in order to avoid the formation of defective oligonucleotide chains. No waiting time is to be observed after the addition of the capping reagents, since these reagents react extremely rapidly.

The capping operation is followed by a third washing operation carried out analogously to the second washing operation, again for a period of time of about 15 seconds.

The third washing operation is followed, by closing the valve 88 and opening the selector valve 80 assigned to the reservoir container 86 for iodine solution, by an oxidation operation, in that the iodine solution is fed from the reservoir container 86 through the opened feed valves 38 to the reaction vessels 20 for about 2 seconds. This oxidation operation stabilizes the phosphate foundation matrix of the oligonucleotide chains by oxidation of the phosphorus from P(III) to P(V).

Finally, a fourth washing operation is carried out for 15 seconds analogously to the second and the third washing operation, in order to rinse the iodine solution out of the reaction vessels 20. One run of the insert 18 in question is thus ended, and can be followed by further runs in order to produce the desired nucleotide chains. When the required number of circulations per insert 18 has taken place, the corresponding insert can be removed from the rotary plate 16 from the side and replaced by a new insert 18 containing initiator bases.

Figure 3:
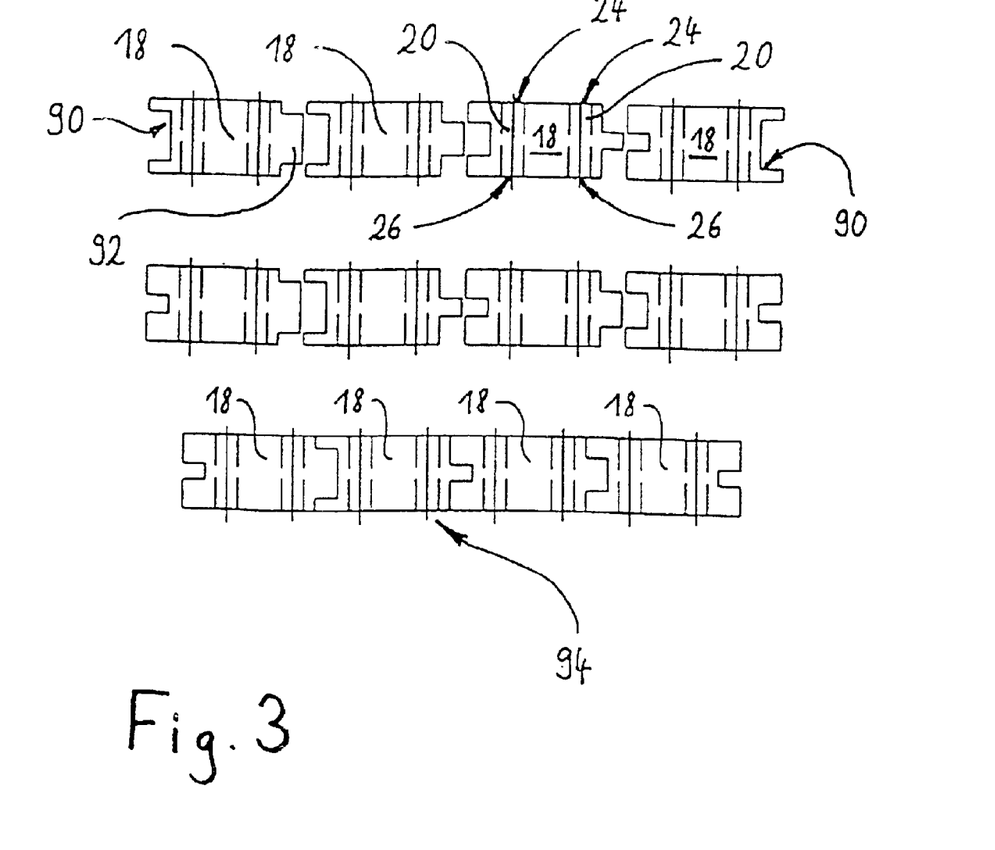
FIG. 3 shows a row of differently coded inserts, of which in each case four can be combined to a reaction vessel panel in MTP format.

The inserts 18 are explained in more detail in FIGS. 2 and 3. Each insert 18 is substantially bar-shaped and has two rows of reaction vessels 20 parallel to one another, for example 12 reaction vessels per row. On its longitudinal sides each insert 18 is provided with at least one coding groove 90 or with at least one coding projection 92. These coding grooves 90 and/or coding projections 92 ensure that a particular insert 18 can be inserted into the rotary plate 16 only at a particular position, namely at that position at which the rotary plate 16 has coding grooves 90' (not shown) or coding projections 92' which correspond to the coding grooves 90 or the coding projections 92 of the particular insert 18. Incorrect charging of the rotary plate 16 is therefore virtually ruled out.

As a further advantage, the inserts 18 constructed in such a manner can be assembled to form reaction vessel panels 94 in standard MTP format (see FIG. 3), this also being possible only in a particular sequence determined by the coding grooves 90 and coding projections 92 of the corresponding inserts 18.

Figure 4:
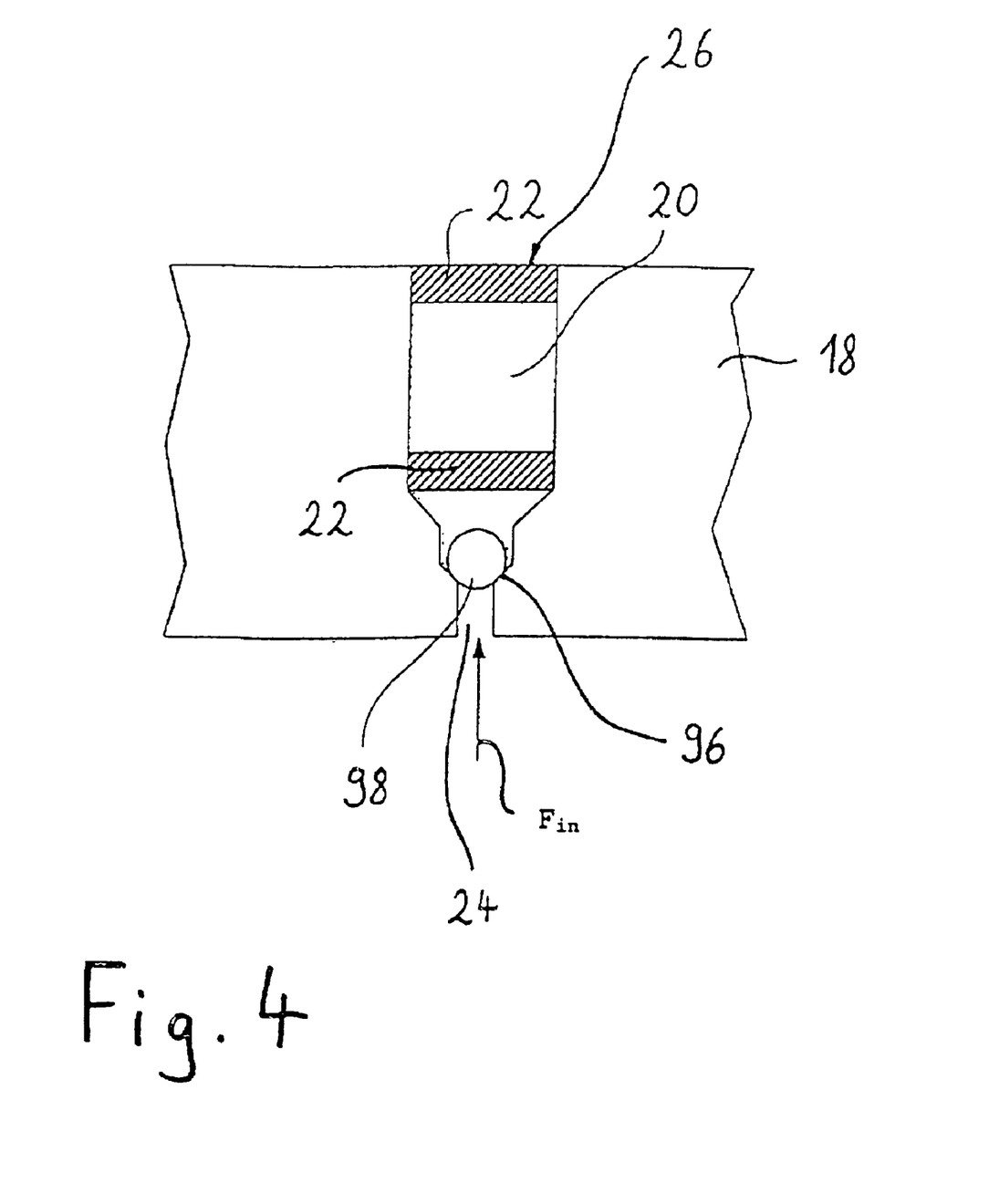
FIG. 4 shows a particular closing device for the reaction vessel outlet or reaction vessel inlet of a reaction vessel.

FIG. 4 shows, in cross-section, a reaction vessel 20 constructed in an insert 18 with a reaction vessel inlet 24 arranged at the bottom and a reaction vessel outlet 26 arranged at the top and two frit bases 22 arranged between the inlet 24 and the outlet 26. The frit bases 22 form the boundary of the actual reaction chamber, in that they are permeable to reaction liquids but do not allow the oligonucleotides to escape from the reaction chamber.

During a relative movement between the reaction vessels 20 and the four stations 28, 30, 32 and 34 of the device 10, the reaction vessels 20 are uncoupled from the feed and drain, i.e. there is no liquid connection between a feed line and the reaction vessel inlet 24 and between a removal line and the reaction vessel outlet 26. The liquid in the reaction vessel 20 can therefore tend to run out because of the force of gravity acting on it.

To prevent this, according to one embodiment of the device 10 each reaction vessel 20 is provided with a special closing device 95 for the reaction vessel inlet 24 lying underneath it. This closing device 95 comprises a constriction point 96 arranged in the reaction vessel inlet 24, which can be closed by a ball 98 which can move to and fro and is also arranged in the reaction vessel inlet 24.

In the embodiment example shown in FIG. 4, the ball 98 is pushed by the force of gravity against the constriction point 96. Alternatively or additionally, however, the ball 98 can also be pushed in the direction of the constriction point 96 by a spring or by magnetic forces. It goes without saying that the force pushing the ball 98 in the direction of the constriction point 96 must be smaller than the force acting in the direction of the arrow $F_{in}$ when liquid flows through the reaction vessel inlet 24, so that the reaction vessel inlet 24 opens.

The closing device 95 reliably prevents liquid from running out of the reaction vessel 20 after a feed line has been uncoupled from the reaction vessel inlet 24. Although only one closing device 95 assigned to the reaction vessel inlet 24 is shown in FIG. 4, in other embodiments such a closing device 95 is also present at the reaction vessel outlet 26, in order to prevent, for example, air from penetrating into the reaction vessel 20 when the reaction vessel 20 is uncoupled.

Figure 5:
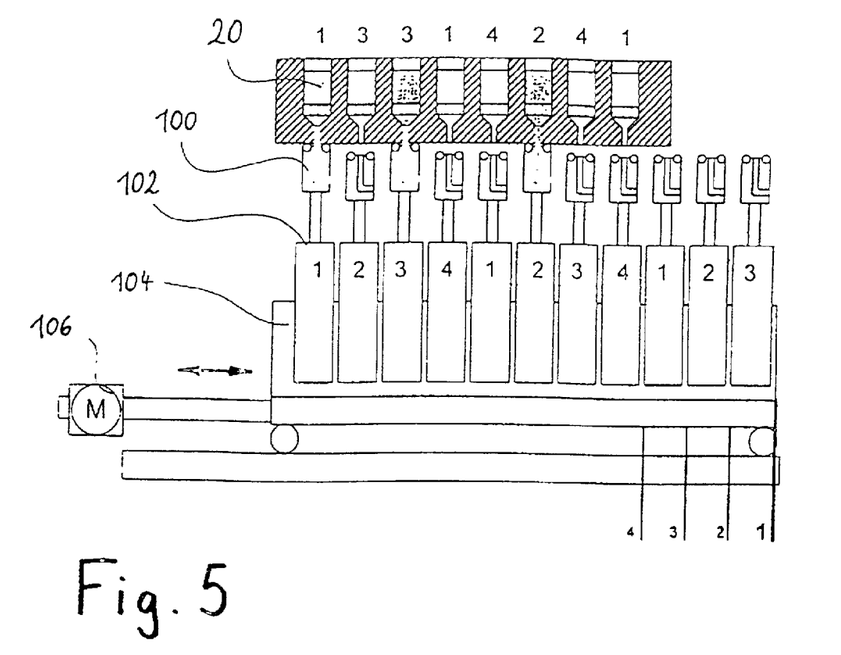
FIG. 5 shows a particular embodiment of a liquid feed device of the device according to the invention.
Figure 6:
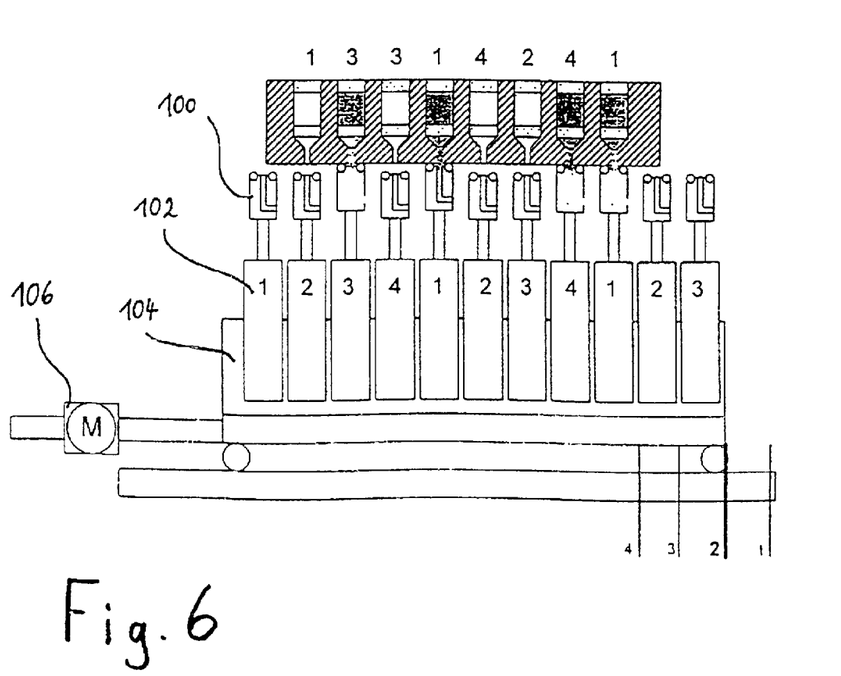
FIG. 6 shows a particular embodiment of a liquid feed device of the device according to the invention.

FIGS. 5 and 6 show a special liquid feed device 36 such as is used advantageously at the third station 32 of the device 10 in particular. In the embodiment example shown, this liquid feed device 36 has eleven individual feeds 100, each of which is in liquid connection with only one of the liquids to be added to the reaction vessels 20 at the station. The minimum number of individual feeds 100 corresponds to the number of different liquids which are to be added at the particular station. Preferably, however, more individual feeds 100 than this minimum number are present, so that the corresponding liquid can be fed faster to the reaction vessels 20 in a station.

Each individual feed 100 is mounted on a coupling drive 102, which, when the individual feed 100 is under the correct reaction vessel inlet 24, can couple it to this reaction vessel inlet 24. In the embodiment example shown, the coupling drive 102 can move the individual feed 100 assigned to it a distance upwards and downwards, in order to effect coupling to and uncoupling from the reaction vessel 20. The coupling drives 102 are fixed together with the individual feeds 100 on a common carrier 104 which can be displaced at right angles to the reaction vessel inlets 24. In the embodiment example shown, the common carrier 104 is a carriage which can be displaced position by position such that one displacement by one position corresponds to the distance between two adjacent reaction vessel inlets 24.

Functioning of the liquid feed device 36 shown in FIGS. 5 and 6 will now be explained. For better understanding, a number is given above each reaction vessel 20, which symbolizes a liquid to be added to the corresponding reaction vessel. In the same way, a number is given on each coupling drive 102, which symbolizes the liquid with which the corresponding individual feed 100 is in liquid connection. Depending on the position of the carrier 104 constructed as a carriage here, the coupling drives 102 couple to reaction vessels 20 only those individual feeds 100 where the number given on the coupling drive coincides with the number given above the reaction vessel 20. In other words, only those individual feeds 100 which are in fluid connection with the liquid precisely required for the corresponding reaction vessel 20 are coupled. In FIG. 5, from the left, these are the first, the third and the sixth individual feed 100. The other individual feeds 100 remain in the uncoupled position.

When the liquids have been fed in, the associated coupling drive 102 uncouples each individual feed 100 from the reaction vessel inlet 24 again. The carrier 104 constructed as a carriage and driven by a positioning drive 106 then moves, for example to the left by one position (see FIG. 6), so that the individual feeds 100 are now in alignment with other reaction vessels, more precisely reaction vessel inlets 24 thereof, than before. Those individual feeds 100 where the liquid coincides with the liquid to be added to the corresponding reaction vessel are now again coupled with the reaction vessel inlets 24. In FIG. 6 these are the third, the fifth, the eighth and the ninth individual feed 100.

The operation described. i.e. the moving of the carrier 104 position by position, is carried out until the desired liquid has been added to each reaction vessel 20. The carriage 104 can optionally also be displaced by the control with which it cooperates by several positions at once, for example if, after the carriage 104 has been displaced by only one position, there is no agreement between the liquids of the individual feeds 100 and the reaction vessels 20 which are precisely in alignment with these.

Such a liquid feed device 36 enables the particular liquids required to be fed to the reaction vessels 20 without mixing or entrainment of the various liquids occurring. The quality of the oligonucleotides produced is increased as a result.

What is claimed is:

1. A process for the parallel synthesis of at least 4n oligonucleotides, with the steps:
   arrangement of at least four inserts each with n reaction vessels on a plate such that a first insert is at a first station, a second insert is at a second station, a third insert is at a third station and a fourth insert is at a fourth station, each reaction vessel containing an initiator base bound to an inert carrier, or a universal carrier,
   carrying out in parallel of
   a) a deblocking operation to remove protective groups simultaneously in all n reaction vessels of the insert at the first station,
   b) a first washing operation simultaneously in all n reaction vessels of the insert at the second station,
   c) a coupling operation for attaching individual nucleotides in all n reaction vessels of the insert at the third station, and
   d) a second washing operation followed by a capping operation for blocking oligonucleotides which have not undergone the desired chain lengthening in the preceding coupling operation followed by a third washing operation followed by an oxidation operation for stabilizing the phosphate foundation matrix of the oligonucleotides, followed by a fourth washing operation simultaneously in all n reaction vessels of the insert at the fourth station, and
   station by station rotation of the inserts through the four stations mentioned or of the stations relative to the inserts and carrying out of the above-mentioned operations until the desired oligonucleotides have been formed by coupling of the individual nucleotides to one another.

2. The process according to claim 1, wherein at the second station, together with the first washing operation carried out there, a monitoring operation which provides information on the quality of the deblocking operation carried out at the first station takes place.

3. The process according to claim 2, wherein the monitoring operation comprises an on-line measurement of the conductivity of a washing liquid used for the first washing operation.

4. The process according to claim 2, wherein the monitoring operation comprises an on-line measurement of the colour intensity of a washing liquid used for the first washing operation.

5. The process according to claim 4, wherein measurement of the colour intensity is carried out by means of UV light.

6. The process according to claim 2, wherein the first washing operation is carried out until the monitoring operation shows that the protective groups removed in the preceding deblocking operation have been rinsed out completely.

7. The process according to claim 1, wherein in the coupling operation carried out at the third station, a selected nucleotide base is added to the reaction vessels simultaneously with an activator.

8. The process according to claim 1, wherein in the coupling operation carried out at the third station, a marking group is added to the reaction vessels.

9. The process according to claim 8, wherein the marking group is selected from the group consisting of a base analogue, a dyestuff and a hapten.

10. The process according to claim 1, wherein the reaction vessels are constructed as flow-through vessels, each reaction vessel having an inlet and an outlet, and wherein the liquids to be fed to the reaction vessels in the four stations are conveyed into the reaction vessels and out of them by applying a pressure gradient between the reaction vessel inlet and reaction vessel outlet.

11. The process according to claim 1, wherein all the operations are carried out under an inert gas atmosphere.

12. The process according to claim 11, wherein the inert gas atmosphere is selected from the group consisting of nitrogen, argon, and a nitrogen/argon combination.

13. A device for the parallel synthesis of at least 4n oligonucleotides, comprising a first station for carrying out a deblocking operation, a second station for carrying out a first washing operation, a third station for carrying out a coupling operation, a fourth station for carrying out a second washing operation followed by a capping operation followed by a third washing operation followed by an oxidation operation followed by a fourth washing operation, the first, the second, the third and the fourth station following one another at a distance in the circumferential direction, a plate, which has at least four inserts each with n reaction vessels such that a first insert is at the first station, a second insert is at the second station, a third insert is at the third station and a fourth insert is at the fourth station, each reaction vessel being constructed as a flow-through vessel with a reaction vessel inlet and a reaction vessel outlet, a device for carrying out a relative movement station by station between the plate and the stations, a liquid feed device assigned directly to the reaction vessel inlets in each station, and a drain channel assigned directly to each reaction vessel outlet in each station, each reaction vessel inlet being in tight engagement with the associated liquid feed device and each reaction vessel outlet being in tight engagement with the associated drain channel when the inserts are in a station, and there being a small axial distance at least between the reaction vessel inlets and the liquid feed device while a relative movement station by station between the plate and the stations takes place.

14. The device according to claim 13, wherein there is also a small axial distance between the reaction vessel outlets and the drain channels while a relative movement station by station between the plate and the stations takes place.

15. The device according to claim 13, wherein the plate is a rotary plate and wherein all the liquid feed devices are accommodated in or on a valve-carrying panel and all the drain channels are accommodated in a suction panel.

16. The device according to claim 15, wherein the valve-carrying panel has a flat contact surface to the upper side of the rotary plate and the suction panel has a flat contact surface to the underside of the rotary plate, and wherein the reaction vessel inlets are constructed flush with the upper side of the rotary plate and the reaction vessel outlets are constructed flush with the underside of the rotary plate.

17. The device according to claim 15, wherein the valve-carrying panel and the suction panel are fixed against rotation, and wherein the rotary plate and the suction panel can be lowered relative to the valve-carrying panel.

18. The device according to claim 13, wherein each liquid feed device has n feed valves.

19. The device according to claim 13, wherein each insert extends radially in the plate and has at least one row of reaction vessels.

20. The device according to claim 19, wherein each insert has two rows of reaction vessels parallel to one another.

21. The device according to claim 13, wherein the inserts are made of plastic.

22. The device of claim 21, wherein the inserts are made of polyether ether ketone.

23. The device according to claim 13, wherein each insert has on its longitudinal sides a coding groove of different construction or a coding projection which cooperates with a corresponding coding projection or a corresponding coding groove of the rotary plate.

24. The device according to claim 23, wherein the inserts can be assembled to reaction vessel panels by means of the coding grooves and the coding projections.

25. The device according to claim 13, wherein the reaction vessel outlet and/or the reaction vessel inlet of each reaction vessel has a constriction point which can be closed by a movable ball.

26. The device according to claim 25, wherein the ball is pushed in the direction of the constriction point by a force selected from the group consisting of gravity, the force of a spring, and magnetic force.

27. The device according to claim 13, wherein at least the liquid feed device of the third station has a plurality of individual feeds, each of which is in liquid connection with the only one of the various liquids to be added to the reaction vessels at the station and the number of which corresponds to at least the number of different liquids to be added to the reaction vessels at the station, a coupling drive for the individual feeds in order to connect each individual feed with a reaction vessel inlet as required, and a common carrier for the individual feeds which can be displaced at right angles to the reaction vessel inlets.

28. The device according to claim 27, wherein the carrier is constructed as a carriage which can be displaced position by position, each reaction vessel inlet representing a position.

29. The device according to claim 27, wherein the coupling drive in a position of the carrier in which individual feeds are in alignment with reaction vessel inlets connected to a reaction vessel inlet only that individual feed which is connected to the liquid precisely required in the reaction vessel in question, and wherein, depending on the requirement, the carrier is then displaced optionally several times into another position in which individual feeds are in alignment with reaction vessel inlets and in which in turn the coupling drive connects to a reaction vessel inlet only that individual feed which is connected to precisely the liquid required in the reaction vessel in question.

* * * * *